United States Patent [19]

DeVries

[11] Patent Number: 4,640,831

[45] Date of Patent: Feb. 3, 1987

[54] METHOD FOR RECOVERING PROTIC ACIDS USING REVERSIBLE BASES

[75] Inventor: Robert A. DeVries, Midland, Mich.

[73] Assignee: The Dow Chemical Company, Midland, Mich.

[21] Appl. No.: 683,439

[22] Filed: Dec. 18, 1984

[51] Int. Cl.[4] .......................... C01B 7/01; C01B 7/19; C01B 9/08

[52] U.S. Cl. .................................. 423/481; 423/483; 423/488

[58] Field of Search ............... 423/488, 226, 228, 481, 423/483

[56] References Cited

U.S. PATENT DOCUMENTS

| | | | |
|---|---|---|---|
| 2,946,652 | 7/1960 | Bloch | 423/228 |
| 3,116,306 | 12/1963 | Heck | 260/410.9 |
| 3,457,299 | 7/1969 | Closson et al. | 260/486 |
| 3,545,916 | 12/1970 | Deichev et al. | 423/228 |
| 3,626,005 | 12/1971 | Scheben et al. | 260/544 A |
| 3,636,082 | 1/1972 | Knowles | 260/475 R |
| 3,656,887 | 4/1972 | Suzuki et al. | 423/226 |
| 3,960,932 | 6/1976 | Heck | 260/479 R |
| 3,966,785 | 6/1976 | Bratzler et al. | 423/220 |
| 3,988,358 | 10/1976 | Heck | 260/465 D |
| 3,991,101 | 11/1976 | Knifton | 260/486 AC |
| 4,112,049 | 9/1978 | Bozzelli et al. | 423/226 |
| 4,112,050 | 9/1978 | Sartori et al. | 423/223 |
| 4,112,052 | 9/1978 | Sartori et al. | 423/228 |
| 4,115,530 | 9/1978 | Coenen et al. | 423/488 |
| 4,217,237 | 8/1980 | Sartori et al. | 252/192 |
| 4,217,238 | 8/1980 | Sartori et al. | 252/192 |
| 4,230,681 | 10/1980 | Coenen et al. | 423/481 |
| 4,272,502 | 6/1981 | Ziegenbein et al. | 423/488 |
| 4,291,007 | 9/1981 | Baniel | 423/488 |
| 4,296,078 | 10/1981 | Tellis | 423/488 |
| 4,334,042 | 6/1982 | Matsumoto et al. | 525/339 |
| 4,360,363 | 11/1982 | Fervin et al. | 423/228 |
| 4,405,578 | 9/1983 | Sartori et al. | 423/223 |
| 4,405,581 | 9/1983 | Sauage et al. | 423/226 |

FOREIGN PATENT DOCUMENTS 0031200 7/1981 European Pat. Off. .
1091042 11/1967 United Kingdom .

Primary Examiner—Gregory A. Heller
Attorney, Agent, or Firm—Norman L. Sims

[57] ABSTRACT

The invention is a process for the recovery of protic acids from a medium which comprises
(a) contacting a medium containing a protic acid with a reversible base under conditions such that the protic acid and the reversible base form a salt; and
(b) exposing the salt of the protic acid and the reversible base to temperatures at which the salt dissociates liberating the protic acid.

16 Claims, No Drawings

METHOD FOR RECOVERING PROTIC ACIDS USING REVERSIBLE BASES

BACKGROUND OF THE INVENTION

This invention relates to the recovery of protic acids from a medium containing such acids. More particularly, this invention relates to a method of separating a protic acid from a medium and then recovering the protic acid in a usable form.

There are many processes wherein protic acids are generated. In most of these processes it is desirable to recover the protic acids. In certain processes, the protic acid is part of a waste stream and failure to recover the acid from the waste stream results in environmental damage. In other processes, the acid is a valuable chemical which can be used for further chemical processing, or can be recycled in the process. Thus, there is a need to recover such protic acids from waste streams or from reaction media. One common method is to contact the acid with an amine or a basic compound such as an alkaline earth metal base or alkali metal base, to form a salt. There are several problems with this kind of process. First, in some of these processes, it is very hard to have complete recovery of the acid from the system, as the salt formed may be hard to recover or not all of the acid reacts with the base. In the case of the use of alkali metal or alkaline earth metal bases, the halogen value cannot be recovered in usable form. When an amine is used to recover the acid the amine may decompose when one tries to recover the acid from the base. In such cases, it has been found that the dissociation conditions are more harsh than the conditions at which the amine used to recover the acid undergoes decomposition. In either case where the salt is lost, the acid is lost, or the amine undergoes decomposition before the acid can be recovered in the acid form significant cost penalties are paid.

What is needed is a process for the recovery of a protic acid from a medium containing such acid wherein the acid can be easily regenerated without loss or decomposition of the compound used to perform such recovery.

SUMMARY OF THE INVENTION

The invention is a process for the recovery of protic acids from a medium which comprises (a) contacting a medium containing a protic acid with a reversible base under conditions such that the protic acid and the reversible base form a salt; and (b) exposing the salt of the protic acid and the reversible base to temperatures at which the salt dissociates liberating the protic acid.

The process of this invention allows the recovery of a protic acid from a medium and the regeneration of the protic acid in a usable form without significant loss of acid values or the reversible base used to recover the protic acid from the medium.

DETAILED DESCRIPTION OF THE INVENTION

Reversible base refers herein to an aromatic compound, which has one or more nitrogen atoms in an aromatic ring, or a polymer with pendant aromatic compounds having one or more nitrogen atoms in an aromatic ring, wherein the nitrogen atom is sterically hindered in a manner such that the salt formed by the nitrogen atom of the aromatic compound and a strong protic base will undergo dissociation to the aromatic compound and the protic acid at a temperature below the decomposition temperature of the aromatic compound.

Preferred reversible bases are compounds which correspond to one of the formulas

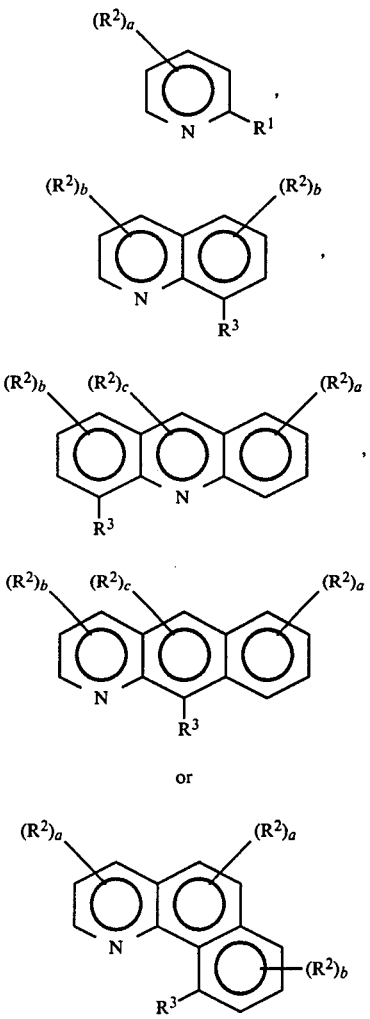

or is a polymer containing units corresponding to one of the formulas

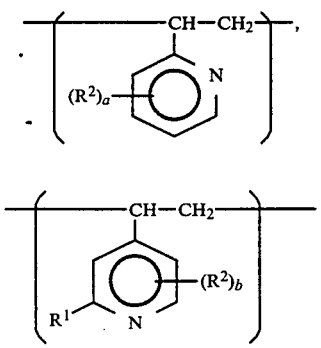

or

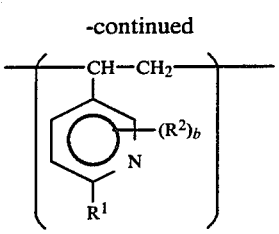

wherein $R^1$ is separately in each occurrence $C_{2-20}$ alkyl, $C_{6-20}$ aryl, $C_{7-20}$ alkaryl, $C_{7-20}$ aralkyl or $C_{3-20}$ cycloalkyl, wherein the $C_{2-20}$ alkyl, $C_{6-20}$ aryl, $C_{7-20}$ aralkyl, $C_{7-20}$ alkaryl or $C_{3-20}$ cycloalkyl is unsubstituted or substituted with a halo, nitro, cyano, $C_{1-20}$ alkoxy, $C_{6-20}$ aryloxy, $C_{7-20}$ alkaryloxy or $C_{7-20}$ aralkoxy; $R^2$ and $R^3$ are separately in each occurrence $C_{1-20}$ alkyl, $C_{6-20}$ aryl, $C_{7-20}$ alkaryl, $C_{7-20}$ aralkyl, $C_{3-20}$ cycloalkyl, nitro, cyano, halo, $C_{1-20}$ alkoxy, $C_{6-20}$ aryloxy, $C_{7-20}$ alkaryloxy or $C_{7-20}$ aralkoxy wherein the $C_{1-20}$ alkyl, $C_{6-20}$ aryl, $C_{7-20}$ alkaryl, $C_{7-20}$ aralkyl, $C_{1-20}$ alkoxy, $C_{6-20}$ aryloxy, $C_{7-20}$ alkaryloxy, $C_{7-20}$ aralkoxy or $C_{3-20}$ cycloalkyl group is unsubstituted or substituted with a halo, nitro, cyano, $C_{1-20}$ alkoxy, $C_{6-20}$ aryloxy, $C_{7-20}$ alkaryloxy or $C_{7-20}$ aralkoxy;

a is separately in each occurrence an integer of from 0 to 4;

b is separately in each occurrence an integer of from 0 to 3;

c is separately in each occurrence the integer 0 or 1; and d is separately in each occurrence the integer of from 0 to 2. Examples of preferred reversible bases include 2,4,6-tri-t-butylpyridine, 2,6-di-t-butyl-4-methylpyridine, 2,6-di-t-butylpyridine, 2-t-butylpyridine, 2-benzylpyridine, 2,6-diphenylpyridine, 2-phenylpyridine, 2,6-dimethoxypyridine, 2-phenoxypyridine, 2,6-diphenoxypyridine, 2-methylquinoline, 6-methylquinoline, 7,8-benzoquinoline, and the like. More preferred reversible bases include 2,4,6-tri-t-butylpyridine, 2,6-di-t-butyl-4-methylpyridine, 2,6-di-ti-butylpyridine, 2-t-butylpyridine, 2-benzylpyridine, 2,6-diphenylpyridine, 2-phenylpyridine, 2-phenoxypyridine, 2,6-diphenoxypyridine and 2,6-dimethoxypyridine.

It is preferred that the bases used for this invention have a purity of above 90 percent, preferably above 95 percent and most preferably above 99 percent by weight. The boiling points of the bases should preferably be at least 20 degrees above the thermal dissociation temperature under dissociation conditions.

The polyvinyl pyridine resins useful in this invention include homopolymers of vinyl pyridine compounds, which are appropriately sterically hindered, and copolymers of vinyl pyridine compounds with 1,2-ethylenically unsaturated compounds, for example, styrene, divinylbenzene, ethylene, vinyl chloride, and the like. Furthermore, the vinyl pyridines may be polymerized with 2 or more of such 1,2-ethylenically unsaturated compounds. Such polymerization processes are well-known in the art, see for example, D'Aelio, U.S. Pat. No. 2,623,013; *Kirk-Othmer Encyclopedia of Chemical Technology*, 3rd Ed., Vol. 21, p. 816 et seq. and Vol. 19, pp. 475-76; references incorporated herein by reference.

In the hereinbefore presented formulas $R^1$ is preferably $C_{3-10}$ alkyl, $C_{6-10}$ aryl, $C_{7-10}$ alkaryl, $C_{7-10}$ aralkyl, $C_{5-10}$ cycloalkyl, $C_{6-10}$ aryloxy and $C_{7-10}$ alkaryloxy. More preferably $R^1$ is $C_{3-10}$ alkyl, $C_{7-10}$ alkaryloxy, $C_{6-10}$ aryloxy or $C_{6-10}$ aryl; $R^1$ is most preferably isopropyl, isobutyl, t-butyl, phenoxy, or phenyl. $R^2$ is preferably halo or $C_{1-10}$ alkyl. $R^2$ is more preferably $C_{1-3}$ alkyl. $R^3$ is preferably $C_{2-10}$ alkyl, $C_{6-10}$ aryl, $C_{6-10}$ aryloxy or $C_{7-10}$ alkaryloxy. $R^3$ is more preferaby $C_{3-10}$ alkyl, phenoxy or phenyl. $R^3$ is most preferably isopropyl, isobutyl, t-butyl, phenoxy or phenyl. Preferably, a is an integer of from 0 to 2, and most preferably 0 or 1. Preferably, b is an integer of 0 or 1. Preferably, d is an integer of 0 or 1.

This process is useful for recovering any compound that has an acidic proton which is capable of forming a salt or associated compound with a thermally reversible base. A preferred class of acids are the strong protic acids. More preferred acids include hydrofluoric acid, hydrobromic acid, hydrochloric acid, hydroiodic acid, sulfuric acid, sulfonic acid, nitric acid, nitrous acid, phosphoric acid, carboxylic acids, phosphonic acids, mercaptans, hydrogen cyanide, trinitromethane, hydrogen sulfide and dinitromethane. Even more preferred acids include hydrochloric acid hydrofluoric acid, hydrobromic acid, hydroiodic acid, hydrogen sulfide, sulfuric acid, sulfurous acid, nitric acid, nitrous acid, phosphorous acid, or carboxylic acids. Even more preferred acids include hydrobromic acid, hydrochloric acid, acetic acid, or trifluoroacetic acid. The most preferred acid is hydrobromic acid.

The medium from which the acid is recovered can be any medium in which an acid is present or in which an acid is generated. That medium can be a gaseous mixture which either contains an acid or in which an acid is generated. Alternatively, the medium can be a liquid which contains an acid or wherein an acid is generated. In some embodiments the medium may be a reaction mixture in which the acid is generated by the reaction performed, wherein the recovery of or tying up of the acid is desirable. Specific examples of mediums which are useful in this invention include waste streams from organic processes, gaseous reaction mixtures, liquid reaction mixtures, gases in a smoke stack, and the like.

In general, the acid-containing medium is contacted with the reversible base under conditions such that a salt of the acid and the reversible base is formed. In particular, an acid-containing gaseous mixture or liquidous mixture can be contacted with the reversible base in a liquid or solid form. The reversible base can either be a liquid, dissolved in a liquid solvent, slurried in a liquid, or can be of a solid form.

In those embodiments wherein the acid is in a gaseous medium, the gaseous medium can be passed over a bed of the reversible base in the solid form, it can be bubbled through the pure reversible base, or a solution of the reversible base; or the gaseous medium containing the acid can be passed through a column countercurrently with the liquid reversible base, or a solution containing the reversible base. In one preferred mode, the contacting is conducted by feeding the gaseous medium into the base of a column while the reversible base-containing liquid is fed into the top of the column, wherein the base-containing liquid flows downward through the column contacting the gaseous medium flowing upward through the column. The gaseous medium freed from the acid emerges from the top. The liquid containing the reversible base and the salt of the reversible base is collected at the bottom of the column.

In those embodiments wherein the medium is a liquid, such medium can be a waste stream containing the acid or a reaction mixture which generates the acid. This liquid medium containing the acid can be passed over a bed of a solid containing the reversible base, alternatively the liquid medium can be passed countercurrently through a tube with the reversible base either in pure liquid form or dissolved in a solvent. In those embodiments wherein the acid is generated in a reaction medium, the base can either be slurried into or dissolved into the liquid reaction medium.

The medium containing the protic acid and the reversible base can be contacted at any temperature at which the salt of the acid and the reversible base is formed. Preferable temperatures for such contacting are between about −50° C. and 150° C. More preferable temperatures for such contacting are between about 0° C. and 100° C.

The ratios of acid to reversible base are not critical to the invention but will affect the rate of salt formation or dissociation. In general, an excess of reversible base is preferred for more complete removal of acid from the medium. The salt is in equilibrium with the acid and reversible base at all times, and under lower temperatures the equilibrium is shifted towards the formation of the salts. In general, the ratio of base to acid can be between about 1:10 and 10:1. Solvents useful for the reversible bases are inert solvents which can be polar or nonpolar. Preferred solvents are inert and have boiling points above or at the desired thermal dissociation temperature. Preferable solvents include organic liquids which under the process conditions are liquid, inert, and which in part dissolve the base and/or the salt. Such solvents include aliphatic, aromatic and cycloaliphatic hydrocarbons. Such hydrocarbons may be substituted with halogen-, ether-, amide- or ketone-containing moieties. Preferred solvents include tetralin, dodecane, tetradecane, xylenes, o-dichlorobenzenes and diphenylene oxide.

The contacting, and recovery of the acid, can be performed at any pressure at which the salt forms and preferably between about 0.013 atmospheres and about 140 atmospheres, more preferably between about 1 and 10 atmospheres.

Once the acid has been recovered from the medium by forming a salt with the reversible base, the salt may optionally be separated from the medium. The salt can be isolated by any conventional means known for separating either a liquid or a solid from a medium. For example, isolation of the solid salt by filtration, purification by rinsing, and vacuum drying is one method. The salt can be separated from a reaction mixture or process stream in solution by extraction or phase separation. It may be recognized that separation of the salt from the reaction mixture may not be necessary and it would be advantageous to directly thermally dissociate and remove the acid from the base or mixture.

The acid values may be recovered from the salt of the reversible base and acid by exposing the salts to temperatures at which the salt undergoes dissociation. Preferred dissociation temperatures are between about 50° C. and 300° C. with between 100° C. and 250° C. being more preferred. In one embodiment, the separated salt can be exposed to the appropriate temperatures for which dissociation occurs. Under another embodiment, the salt can be dissolved in a suitable solvent and heated to reflux of the solvent, provided the reflux temperature is below the decomposition temperature of the reversible base and above the dissociation temperature of the salt. In one preferred embodiment, wherein the medium from which the acid has been recovered is a liquid reaction medium, the liquid reaction medium may be exposed to temperatures at which the salt dissociates and which are below the decomposition temperature of the reversible base. In this embodiment, it is preferred that the reaction solvent be heated to its reflux temperature, thereby liberating the acid. In those embodiments wherein the acid is liberated in a gaseous form, the dissociation may be performed in the presence of an inert sweep gas or under reduced pressure to carry the acid away from the salt so as to drive the equilibrium toward the dissociated acid and base. A lower ratio of base to acid favors dissociation of the salt and recovery of the acid.

It is preferred to perform the dissociation in the absence of oxygen or oxidizing agents.

Another method of dissociation involves contacting the salt of the acid and the reversible base in a countercurrent manner with a hot gas at temperatures at which the salt undergoes dissociation. In this embodiment, the hot gas will carry away any volatilized acid, therefore driving the equilibrium towards the dissociation.

In one preferred embodiment, the process of this invention comprises (a) contacting an organic halide with carbon monoxide and an esterifying agent, in the presence of a Group VIII metal catalyst and a reversible base, under conditions such that an ester is prepared and the hydrogen halide generated during the process forms a salt with the reversible base;

(b) separating the salt of the hydrogen halide and reversible base from the reaction mixture;

(c) dissociating the hydrogen halide from the salt; and (d) recovering the hydrogen halide.

This process allows for the recovery of the halide values generated during the carbonylation process. The halide values can thereafter be recycled to prepare the starting materials for the carbonylation process, therefore resulting in no significant loss of halide values. The base can be recycled for use as an acid acceptor in the carbonylation reaction once the salt of the hydrogen halide and reversible base has dissociated.

Organic halide refers herein to any halogenated organic compound which will undergo carbonylation under carbonylation conditions. Examples of organic halides useful in the invention include aryl halides, heterocyclic halides, vinylic halides, ethynylic halides, benzylic halides or allylic halides, or derivatives thereof.

The organic halide is carbonylated and esterified by contacting it with an esterifying agent and carbon monoxide, in the presence of a Group VIII metal catalyst and the reversible base to prepare an ester. In a preferred embodiment, the organic halide is a 2-halo-1-alkene and the ester produced is an acrylate ester. The reaction wherein R'OH is the esterifying agent and the organic halide is a 2-halo-1-alkene can be represented by the following equation:

$$CH_2=\overset{\overset{\displaystyle X}{|}}{C}-CH_2R + R'OH + CO + A \xrightarrow{\text{catalyst}}$$

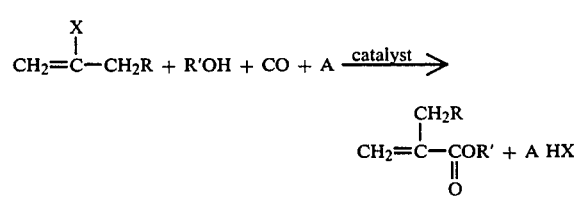

wherein R is hydrogen, alkyl, cycloalkyl or aryl and may be substituted; and R' is aryl, alkyl, cycloalkyl or benzyl and may be substituted with an alkyl, aryl, cycloalkyl, nitro, cyano, ester, carboxylate, amide, aldehyde, hydroxyl, amino, substituted amino quaternized amino or halogen, if these groups are less reactive than the other groups in the reactants which are intended to take part in the reaction; A is a reversible base which is defined hereinbefore; and X is a halogen.

The ester produced is separated from any unreacted materials, the catalyst, the reversible base and any solvent used, by any suitable process, such as distillation.

The esterifying agent used in the esterification of the organic halide may be any alcohol or phenol that has one or more reactive hydroxyl groups. Alcohols and phenols with 1 to 20 carbon atoms or more may be employed. Examples of such alcohols and phenols include paraffinic alcohols and cycloparaffinic alcohols; such as methanol, ethanol, propanol, phenol, cresol, xylenol, naphthol, cyclopentanol and cyclohexanol. Polyols, such as diols and triols may also be used, for example, ethylene glycol and glycerol.

The order of reactivity of alcohols from most to least is primary, secondary and tertiary. R' is preferably a $C_{1-10}$ lower alkyl and substituted or unsubstituted phenol, more preferably R' is a $C_{1-10}$ lower alkyl and most preferably R' is a methyl group.

Carbonates of the formula

and (poly)glycol monoethers of the formula

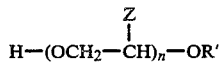

wherein R' is as defined above; n is an integer from 1 to 10; and Z can be, separately in each occurrence, hydrogen or methyl, can also be reacted with the organic halides to prepare the esters. R' is preferably a $C_{1-10}$ lower alkyl and most preferably a methyl group.

Carbon monoxide is added to the reaction by pressurizing the reaction vessel or zone with carbon monoxide gas and maintaining positive pressure with carbon monoxide gas throughout the process. Carbon monoxide can be present in an excess amount. Use of excess carbon monoxide can increase yields. It is desirable to employ from about 1.0 to about 25 or more moles of carbon monoxide per each mole of 2-halo-1-alkene. A preferred amount is from about 1 to about 15 moles.

The esterifying compound used to esterify the organic halide should be present in an equivalent ratio of the former to the latter of at least 1:1.

The catalyst is some form of a Group VIII metal. Preferred Group VIII metals are palladium, cobalt, rhodium, iridium, nickel or platinum, with palladium most preferred. The metals can be employed either as homogeneous or heterogeneous catalysts. Homogeneous catalysts are preferred when the reaction is run in the liquid phase.

When the Group VIII metals are employed as heterogeneous catalysts, either the metal or a salt of the metal is supported on an inert carrier of activated carbon, silica alumina, silica gel, silicalite, activated clays, ion-exchange resins, ligand functionalized ion-exchange resins or titanium, zirconium, magnesium, aluminum or silicon, or oxides thereof. Alumina supports are preferred.

These supported catalysts can be prepared by conventional means, well-known to the art. The palladium on support shows better catalytic activity where the catalyst is prepared from palladium chloride salt. Reduction temperatures between about 230° C. and 300° C., are preferred and give a more active catalyst.

Where palladium is used as the catalyst, between about 0.1 and 10 percent by weight of the support of palladium can be used, preferably between about 0.1 and 2.0 percent by weight of the support.

The reaction temperature is between about 150° C. and 300° C. for a heterogeneous catalyst, preferably between about 220° C. and 250° C. Pressure should be between about 100 and 5000 psi, preferably between about 400 and 1000 psi.

The Group VIII metal can also be used in a homogeneous catalyst. In this form the metal is used in a complex in which the metal can be reduced to the zero valence state, as it is believed that the catalytic species of these metals are the zero valent species. The precursor to the complex can be represented by the formula $Y_mB(LR_3'')_p$ wherein B is a Group VIII metal; Y is chlorine, bromine, iodine, fluorine, acetate or $NO_3$ and the like; L is nitrogen, phosphorus or arsenic; m is an integer between 0 and 2; p is an integer between 0 and 4; and R'' is separately in each occurrence, alkyl, aryl, alkoxy, aryloxy, thioalkyl, thioaryl or acetate.

L is preferably phosphorus; R is preferably alkyl, aryl or acetate; and B is preferably palladium, cobalt, rhodium, iridium, nickel or platinum and most preferably palladium. Both m and p are preferably 2.

These complexes may be prepared in situ, or prior to being added to the reaction. When palladium is used, between about 0.01 and 10 mole percent can be used, between about 0.1 and 1.0 mole percent is preferred.

The temperature for this reaction with a homogeneous catalyst is between about 50° C. and 200° C., preferably 100° C. and 160° C. Below 50° C., the reaction rate is too low, above 160° C. can be detrimental to some catalysts.

The preferred method of carbonylation and esterification of a 2-bromo-1-alkene is a liquid phase reaction with a homogeneous catalyst.

The presence of oxygen can be detrimental to this reaction.

The carbonylation and esterification step may be run in the presence of a solvent. The solvent can be an excess of the alcohol, carbonate, (poly)glycol, (poly)-glycol monoether tertiary amines or the reversible base, which are present either to esterify the carbonylated 2-halo-1-alkene, or present as a halogen acceptor. Alternatively, this step may be carried out in the presence of an inert solvent such as a hydrocarbon or a (poly)glycol diether. The hydrocarbons employed can be either aliphatic, alicyclic or aromatic. Suitable solvents include cyclohexane, benzene, toluene, isooctane, xylene, mesitylene, ether, kerosene, No. 9 oil, 1,3,5-hexanetriether and (poly)alkylene glycol diethers. Of the above-described solvents, those with a boiling point above 160° C. are preferred. Ethylene glycol dimethyl ether or diphenyl oxide are preferred solvents for use with the homogeneous catalyst.

In one embodiment where the 2-halo-1-alkene is 2-chloropropene or 2-bromopropene and the alcohol is methanol, the ester prepared is methyl methacrylate. In one embodiment where the haloalkene is vinyl chloride or vinyl bromide and the alcohol is butanol, the ester prepared is butyl acrylate.

The base formed from the hydrogen halide and the reversible base can be separated from the carbonylation reaction mixture in several ways. In one embodiment wherein the salt is a solid, the solid may be filtered off. The salt can therefore be dissociated by exposing it to temperatures at which the dissociation occurs. In another embodiment wherein the base is dissolved in the reaction mixture after the product has been stripped away, the reaction mixture may be exposed to temperatures at which the reaction mixture refluxes. If that temperature is above the dissociation temperature of the salt, the acid will dissociate and volatilize so as to be carried away from the reaction mixture. The acid can be recovered and recycled for use in preparing the starting material for this reaction, that is, the organic halide.

Alternatively, the salt can be removed from a solution containing the reaction solvent, free base and catalyst by extraction with water. The water can thereafter be removed from the salt by distillation, and the salt can be dissociated thermally.

The reversible bases of this invention are also useful for tying up the acids generated in other carbonylation processes, and thus allowing the recovery of such acids in useful form. In particular, the reversible bases are useful for the recovery of acid values from a process for the preparation of aldehydes by the carbonylation of organic halides with carbon monoxide in hydrogen as described in Heck, U.S. Pat. No. 3,960,932 (incorporated herein by reference). The reversible bases are further useful in the preparation of carboxylic amides by the carbonylation of organic halides and amidation of the carbonylated products with a primary or secondary amine, as described in Heck, U.S. Pat. No. 4,128,554 (incorporated herein by reference). The reversible bases are also useful in olefinic substitution reactions wherein an organic halide is contacted with an olefin in the presence of a group VIII metal catalyst.

SPECIFIC EMBODIMENTS

The following examples are included for illustrative purposes only, and do not limit the scope of the invention or the claims. Unless otherwise stated, all parts and percentages are by weight.

EXAMPLE 1

Preparation of 2,6-diphenylpyridine hydrobromide (not an example of the invention)

Hydrogen bromide gas is introduced into a solution of 30 g (0.130 mole) of 2,6-diphenylpyridine in 150 ml of toluene. The solid which forms is isolated by vacuum filtration. The filtrate is retreated with hydrogen bromide until no more solid is formed. The solid is then dried in vacuo. The product has a melting point of 161° C.-162° C.

EXAMPLE 2

Determination of the hydrogen bromide content of 2,6-diphenylpyridine hydrobromide (not an example of the invention)

To a solution of 6 ml of 0.5 N sodium hydroxide in 100 ml of water is added 0.5028 g of 2,6-diphenylpyridine hydrobromide. Approximately 100 ml of toluene is added and the two-phase mixture is vigorously stirred for one hour. The aqueous layer is removed and titrated with 0.2 N hydrochloric acid to a phenolphthalein endpoint. A total of 6.70 ml of 0.2 N hydrochloric acid is added to reach the endpoint. This corresponds to a 1:1.04 2,6-diphenylpyridine:hydrogen bromide ratio in the salt.

EXAMPLE 3-9

Thermal decomposition of reversible base-hydrogen bromide salts

Procedure:

A 100-ml 1-neck round-bottom flask with a thermocouple and magnetic stir bar is charged with a hydrogen bromide salt of a reversible base, and 50 ml of tetradecane. A Claisen adaptor with a nitrogen inlet tube which protrudes below the liquid level is connected to the flask. To the other end of the Claisen adaptor is attached a Dean-Stark trap fitted with a condenser containing a gas inlet adaptor. The gas inlet adaptor is connected via Tygon tubing to a gas dispersion tube in a cylinder charged with 6.00 ml of 5 N sodium hydroxide solution and approximately 100 ml of water. With a flow of nitrogen through the system (about 300 $cm^3$/min) the reaction mixture is heated progressively to higher temperatures where the temperature was maintained for one-hour periods. The caustic traps are changed for each one-hour period. The solutions in the caustic traps are titrated with 0.2 N hydrogen chloride to a phenolphthalein endpoint to determine the amount of hydrogen bromide liberated. Table I indicates the particular salt, ratio of hydrogen bromide to reversible base, the temperatures and the hydrogen bromide recovery for the hour at each temperature.

TABLE I

| Example | HBr:Amine | % HBr Recovery/hr | | | |
|---|---|---|---|---|---|
| | | RT | 125° C. | 175° C. | 225° C. |
| 1 DPP—HBR | 1.04 | 4.8 | 80.9 | 14.3 | 3.6 |
| 2 PP—HBr | 0.99 | 1.0 | 5.8 | 23.2 | 37.3 |
| 3 BP—HBr | 0.99 | 1.0 | 2.0 | 12.9 | 43.0 |
| 4 TBP—HBr | 1.35 | 0.5 | 79.6 | 11.1 | 1.0 |
| 5 DBMP—HBr | 1.26 | 1.0 | 66.0 | 21.4 | 0.5 |
| 6 C—HBr | 1.00 | 0.8 | 0 | 0.8 | 4.9 |
| 7 TOA—HBr | 1.00 | — | — | — | 18.1 |

RT - room temperature
DPP - 2,6-diphenylpyridine-HBr
PP—HBr - 2-phenylpyridine-HBr
BP—HBr - 2-benzylpyridine-HBr
TBP—HBr - 2,4,6-tributylpyridine-HBr
DBMP—HBr - 2,4-di-t-butyl-4-methylpyridine-HBr
C—HBr - 2,4,6-collidine-HBr
TOA—HBr - tri-n-octylamine-HBr Examples 3–6 show that large sterically hindering groups substantially increase the hydrogen bromide recovery while methyl groups are barely capable of causing thermal cleavage when such are present, and that one large sterically hindering group will also allow for substantial hydrogen bromide recovery although at slightly higher temperatures. Without any sterically hindering groups, there is no significant hydrogen bromide dissociation in a normal pyridine pKa range of 4–6. Example 7 shows that when a trialkylamine-hydrogen bromide salt is thermally dissociated, hydrogen bromide is recovered with significant decomposition of the base to ammonium bromide, primary and secondary ammonium bromides with the formation of 8 carbon bromides and olefins.

EXAMPLE 10

To a stirred high pressure reactor is added 29.57 g of 2,6-di-t-butyl-4-methylpyridine, 1.30 g of dichlorobis(-triphenylphosphine)palladium, 40.73 g of methanol, and 15.72 g of 2-bromopropene. The reactor is pressurized to 375 psig with carbon monoxide, heated to 126° C. and stirred for 1 hour. A sample is removed and the results by analytical gas chromatograph showed 96.5 percent conversion of 2-bromopropene and 81 percent selectivity to methyl methacrylate.

In a glass round-bottom flask fitted with stir bar, gas inlet tube and reflux condenser is added 4.0 g of 2,6-di-t-butyl-4-methylpyridine hydrobromide in 27.72 g of dodecane (boiling point 215° C.). The salt slurry is stirred for 3 hours between 125° C. and 215° C. under a low nitrogen purge which is trapped and passed through water. Titration of the water takes 25.05 ml of 0.5 N sodium hydroxide. Approximately 0.39 g of white solid forms in the condenser which is identified as the salt. Correcting for the salt in the condenser, this corresponds to 99.4 percent recovery of hydrogen bromide.

Isolation of methyl methacrylate:

The crude carbonylation product is vented to remove carbon monoxide, and distilled to remove residual 2-bromopropene and the methyl methacrylate/methanol azeotrope (approximately 65° C.). The low temperature minimizes polymerization. The methyl methacrylate/methanol azeotrope is broken by adding water which separates the azeotrope into a top phase which is pure methyl methacrylate and a lower phase comprised of methanol and water.

This example demonstrates that a reversible base is useful in recovering the halogen value from a carbonylation reaction.

What is claimed is:

1. A process for the recovery of protic acids from a medium which comprises
   (a) contacting a medium containing a protic acid selected from the group consisting of hydrobromic acid, hydrochloric acid, hydrofluoric acid, and hydroiodic acid which comprises hydrobromic acid, hydrochloric acid, hydrofluoric acid, or an hydroiodic acid with a reversible base under conditions such that the protic acid and the reversible base form a salt; and
   (b) exposing the salt of the protic acid and the reversible base to temperatures at which the salt dissociates liberating the protic acid;

wherein the reversible base is a compound corresponding to one of the formulas

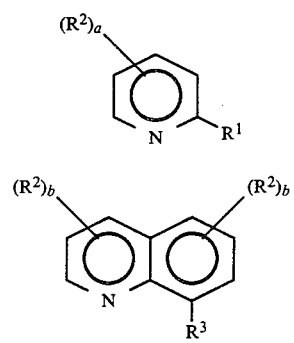

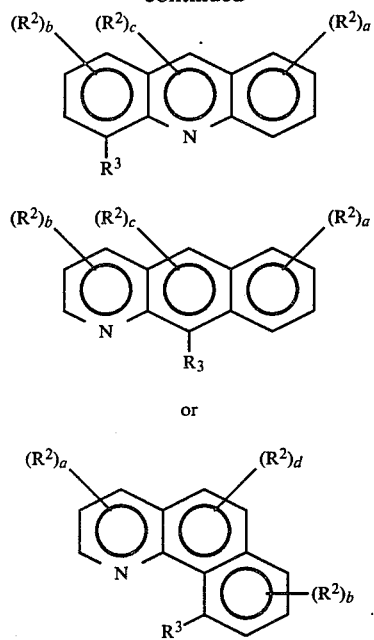

or is a polymer containing units corresponding to one of the formulas

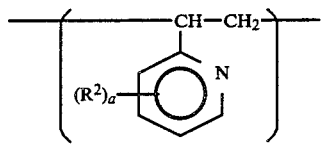

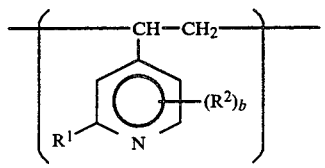

or

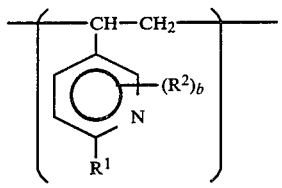

wherein $R^1$ is separately in each occurrence $C_{2-20}$ alkyl, $C_{6-20}$ aryl, $C_{7-20}$ alkaryl, $C_{7-20}$ aralkyl or $C_{3-20}$ cycloalkyl, wherein the $C_{2-20}$ alkyl, $C_{6-20}$ aryl, $C_{7-20}$ aralkyl, $C_{7-20}$ alkaryl or $C_{3-20}$ cycloalkyl is unsubstituted or substituted with a halo, nitro, $C_{1-20}$ alkoxy, $C_{6-20}$ aryloxy, $C_{7-20}$ alkaryloxy or $C_{7-20}$ aralkoxy;

$R^2$ and $R^3$ are separately in each occurrence $C_{1-20}$ alkyl, $C_{6-20}$ aryl, $C_{7-20}$ alkaryl, $C_{7-20}$ aralkyl, $C_{3-20}$ cycloalkyl, nitro, halo, $C_{1-20}$ alkoxy, $C_{6-20}$ aryloxy, $C_{7-20}$ alkaryloxy or $C_{7-20}$ aralkoxy wherein the $C_{1-20}$ alkyl, $C_{6-20}$ aryl, $C_{7-20}$ alkaryl, $C_{7-20}$ aralkyl, $C_{1-20}$ alkoxy, $C_{6-20}$ aryloxy, $C_{7-20}$ alkaryloxy, $C_{7-20}$ aralkoxy or $C_{3-20}$ cycloalkyl group is unsubstituted or substituted with a halo, nitro, $C_{1-20}$ alkoxy, $C_{6-20}$ aryloxy, $C_{7-20}$ alkaryloxy or $C_{7-20}$ aralkoxy;

a is separately in each occurrence an integer of from 0 to 4;

b is separately in each occurrence an integer of from 0 to 3;

c is separately in each occurrence the integer 0 or 1; and d is separately in each occurrence the integer of from 0 to 2.

2. The process of claim 1 wherein $R^1$ is $C_{3-10}$ alkyl, $C_{6-10}$ aryl, $C_{7-10}$ alkaryl, $C_{7-10}$ aralkyl, $C_{3-10}$ cycloalkyl, $C_{6-10}$ aryloxy and $C_{7-10}$ alkaryloxy;

$R_2$ is halo or $C_{1-10}$ alkyl;

$R^3$ is $C_{2-10}$ alkyl, $C_{6-10}$ aryl, $C_{6-10}$ aryloxy, $C_{7-10}$ alkaryloxy;

a is an integer of from 0 to 2;

b is an integer of 0 or 1; and d is an integer of 0 or 1.

3. The process of claim 2 wherein $R^1$ is $C_{3-10}$ alkyl, $C_{6-10}$ aryl, $C_{7-10}$ alkaryloxy or $C_{6-10}$ aryloxy;

$R^2$ is $C_{1-3}$ alkyl;

$R^3$ is $C_{3-10}$ alkyl, phenyl or phenoxy; and a is an integer of 0 or 1.

4. The process of claim 3 which comprises (a) contacting an organic halide with carbon monoxide and an esterifying agent, in the presence of a Group VIII metal catalyst and a reversible base, under conditions such that an ester is prepared and the hydrogen halide which comprises hydrobromic acid, hydrochloric acid, hydroiodic acid or hydrofluoric acid generated during the process forms a salt with the reversible base;

(b) separating the salt of the hydrogen halide and reversible base from the reaction mixture;

(c) dissociating the hydrogen halide from the salt; and (d) recovering the hydrogen halide.

5. The process of claim 3 wherein $R^1$ is isopropyl, isobutyl, t-butyl phenoxy or phenyl; and $R^3$ is isopropyl, isobutyl, t-butyl phenoxy or phenyl.

6. The process of claim 3 wherein the acid is hydrobromic acid.

7. The process of claim 6 wherein the medium containing the hydrobromic acid and the reversible base are contacted at a temperature of between about $-50°$ C. and $150°$ C.

8. The process of claim 7 wherein the contacting temperature is between about $0°$ C. and $100°$ C.

9. The process of claim 7 wherein the salt formed from the reversible base and the hydrobromic acid is dissociated at a temperature of between about $50°$ C. and $300°$ C.

10. The process of claim 9 wherein the dissociation temperature is between about $100°$ C. and $250°$ C.

11. The process of claim 9 wherein the salt of the reversible base and hydrobromic acid is separated from the medium before dissociation of the salt.

12. The process of claim 11 wherein the medium which is contacted with the reversible base is a gas containing a hydrobromic acid, a solution containing a hydrobromic acid, or a reaction mixture which contains or generates a hydrobromic acid.

13. The process of claim 12 wherein the salt of the reversible base and the hydrobromic acid is dissociated by exposing the base to temperatures at which dissociation occurs and passing an inert gas over the salt to carry away the liberated acid.

14. The process of claim 12 wherein the salt of the hydrobromic acid and the reversible base is dissociated by contacting the salt with an inert organic liquid, wherein said liquid has a boiling point at or above the dissociation temperature of the salt and below the decomposition temperature of the base, exposing the salt and organic liquid to temperatures at which the salt undergoes dissociation.

15. The process of claim 14 wherein the salt and organic liquid are exposed to temperatures at which the inert organic liquid refluxes.

16. The process of claim 12 wherein the salt of the hydrobromic acid and the reversible base is dissociated by contacting the salt in a countercurrent manner with a hot gas at temperatures at which the salt undergoes dissociation.

* * * * *

UNITED STATES PATENT AND TRADEMARK OFFICE
CERTIFICATE OF CORRECTION

PATENT NO. : 4,640,831

DATED : February 3, 1987

INVENTOR(S) : Robert A. DeVries

It is certified that error appears in the above-identified patent and that said Letters Patent is hereby corrected as shown below:

Col. 2, formula at lines 40-47 should read as follows:

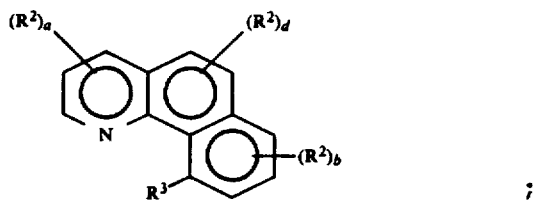

;

Col. 3, line 33, a new paragraph should begin after "2.";

Col. 3, line 41, "2,6-di-butylpyridine" has been misspelled;

Col. 4, line 22, a comma should be inserted after "hydrochloric acid";

UNITED STATES PATENT AND TRADEMARK OFFICE
CERTIFICATE OF CORRECTION

PATENT NO. : 4,640,831

DATED : February 3, 1987

INVENTOR(S) : Robert A. DeVries

It is certified that error appears in the above-identified patent and that said Letters Patent is hereby corrected as shown below:

Col. 11, line 38, Claim 1, after "acids" add -- selected from the group consisting of hydrobromic acid, hydrochloric acid, hydrofluoric acid, and hydroiodic acid --;

Col. 11, lines 41-43, delete "selected from the group consisting of hydrobromic acid, hydrochloric acid, hydrofluoric acid, and hydroiodic acid";

Col. 13, line 16, Claim 2, "$R_2$" should read -- $R^2$ --.

Signed and Sealed this

Thirteenth Day of December, 1988

*Attest:*

DONALD J. QUIGG

*Attesting Officer*        *Commissioner of Patents and Trademarks*